United States Patent [19]

Schlager et al.

[11] Patent Number: 5,278,629
[45] Date of Patent: Jan. 11, 1994

[54] ATOMIC EMISSION SPECTROMETRY

[75] Inventors: Kenneth J. Schlager, Elm Grove; Carl J. Bergrstrom, Milwaukee, both of Wis.

[73] Assignee: Biotronics Technologies, Inc., Waukesha, Wis.

[21] Appl. No.: 28,637

[22] Filed: Mar. 9, 1993

Related U.S. Application Data

[63] Continuation of Ser. No. 729,471, Jul. 12, 1991, abandoned.

[51] Int. Cl.⁵ .................... G01N 21/67; G01N 21/69
[52] U.S. Cl. .................................................. 356/313
[58] Field of Search ................................ 356/311, 313

[56] References Cited

U.S. PATENT DOCUMENTS

| | | | |
|---|---|---|---|
| 2,643,574 | 6/1953 | Todd | 356/313 |
| 2,920,201 | 1/1960 | Annis et al. | 356/313 |
| 3,024,182 | 3/1962 | Furth et al. | 204/193 |
| 3,826,920 | 7/1974 | Woodroffe et al. | 250/373 |
| 4,238,198 | 12/1980 | Swaim et al. | 22/230 |
| 4,330,298 | 5/1982 | Hawn et al. | |
| 4,352,779 | 10/1982 | Parks . | |
| 4,563,331 | 1/1986 | Losee et al. | |
| 4,678,756 | 7/1987 | Parks . | |
| 4,730,111 | 3/1988 | Vestal et al. | 250/280 |
| 4,766,318 | 8/1988 | Alder-Golden et al. | 356/313 |
| 4,814,612 | 3/1989 | Vestal et al. | 250/288 |
| 4,861,989 | 8/1989 | Vestal et al. | 250/281 |
| 4,960,992 | 10/1990 | Vestal et al. . | |
| 4,977,093 | 12/1990 | Cooke et al. . | |
| 5,085,499 | 2/1992 | Griffin et al. | 356/313 |

FOREIGN PATENT DOCUMENTS

| | | | |
|---|---|---|---|
| 927138 | 5/1963 | United Kingdom | 356/313 |
| 933677 | 8/1963 | United Kingdom | 356/313 |

Primary Examiner—F. L. Evans
Attorney, Agent, or Firm—Andrus, Sceales, Starke & Sawall

[57] ABSTRACT

A method and apparatus of atomic emission spectrometry includes confining a solution within an emission chamber for on-line analysis or individual sample analysis. An electrical discharge created within the liquid to directly excite an internal portion of the liquid within the liquid solution. The atomic emission is totally enclosed within a liquid solution pocket. A fiber optic probe is connected directly to the excited internal portion within the liquid and to a suitable analyzer which analyzes the atomic spectral lines to determine the atomic elements within the liquid solution. The system can be used for individual element analysis or a multiple element analysis by use of an array spectrometer, with a simultaneous display of the complete atomic spectrum of multiple elements in a liquid solution, all in less than a period of one second. In an on-line system, the liquid sample flows through the emission chamber with the electrical discharge created as time spaced discharges which are subsequently integrated by the analyzer to produce individual element related signals.

15 Claims, 7 Drawing Sheets

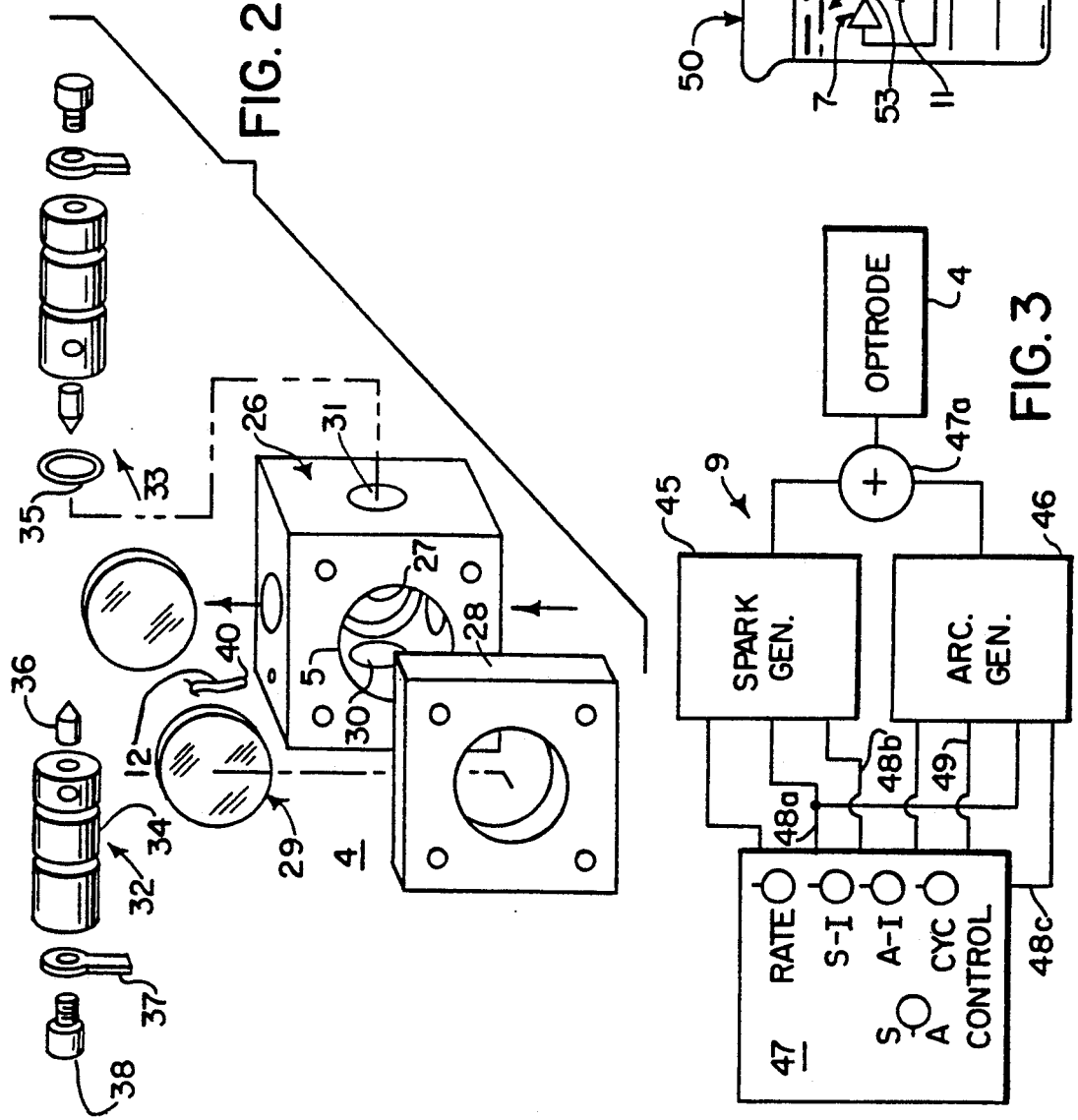

ATOMIC EMISSION SPECTROMETRY

This application is a continuation of Ser. No. 07/729,471, filed Jul. 12, 1991, now abandoned.

BACKGROUND OF THE PRESENT INVENTION

This invention relates to atomic emission spectrometry and particularly to a system adapted for on-line analysis using atomic spectrometry.

Various analytical instrumentations have been developed and suggested for analyzing of solids and liquids. Generally, prior art systems of atomic emission spectrometry require an input of energy for the conversion of the material into a gaseous state. A detailed discussion of the prior art appear in *Spectrochemical Analysis* Published by Prentice Hall and particularly Chapter 9, "Arc and Spark Emission Spectrometry". The materials to be analyzed are in the form of solids or solutions in which the elements being monitored are bonded to other elements. In order to provide for atomic spectrometry analysis, the individual bond must be broken. The atomic elements will emit light in the ultraviolet visible, or near infrared spectral region in response to an appropriate input energy to the element. In addition, each element response is a particular unique element-related frequency. Generally, the input energy has been applied through a plurality of well known different energy sources including 1) flame; 2) electrothermal through the use of a graphite furnace; 3) electric arc; 4) electric sparks and 5) inductively coupled plasma using a radio frequency field. In all instances, the product is converted to a gaseous or plasma condition and the converted gas or plasma is exposed and directly analyzed on a sample-by-sample basis. Each gas or plasma sample is analyzed through light absorption or emission analyses. With atomic absorption, the system measures the light absorbed in the energized atom cell. In atomic emission processes, the light emitted from the energized atom cell is monitored. In atomic fluorescent procedures, the fluorescent light emitted from the energized atom cell is monitored.

For example, U.S. Pat. No. 4,238,198 which issued Dec. 9, 1980 discloses a system for analyzing liquid samples for total inorganic sulfur. The patented system takes a sample of the material and converts it to a volatile $H_2S$ sample which is carried into a plasma chamber using a suitably inert gas. The emitted light of the evolved $H_2S$ is analyzed to determine the total inorganic sulfur concentration within the sample.

Although such methods have been used for atomic emission analysis, the prior art has been significantly limited by the use of sampling procedures including the necessity of converting each sample to a gaseous state and then analyzing of the gaseous product in a separate analysis unit. There is a significant demand for a more direct method for elemental analysis of a liquid solutions, and particularly with a continuous or on-line procedure which eliminates the requirement for sampling.

SUMMARY OF THE PRESENT INVENTION

The present invention is particularly directed to atomic emission spectrometry wherein a liquid medium is directly analyzed, and in a preferred unique process by passing through an emission chamber. An internal gap excitation is created within the liquid solution within the emission chamber. Generally, an arc or spark discharge, hereinafter generally referred to an electrical discharge, is used to directly excite an internal portion within the liquid solution and generate atomic emission totally enclosed within a liquid solution pocket in the chamber. A coupling probe such as a fiber optic light probe is linked to the excited internal portion and coupled to a suitable analyzer. The inventor has found that atomic spectral lines of elemental materials are directly established within the excited internal portion and the spectral light can be detected for direct transmission into the analyzer. The system provides for on-line analysis by eliminating the necessity for sequential sampling as in conventional known modes of atomic spectrometry or conversion and transmission of the converted sample. The new system of this invention can be used for individual element analysis or a multiple element analysis by use of an array spectrometer including known constructions. The present invention thus allows a near simultaneous display of a complete atomic spectrum of multiple elements in a liquid solution, and may operate in less than a period of one second.

Although particularly adapted and unique to provide on-line spectrometry analysis, the method can of course be equally applied to sampled products. Thus, a liquid sample can be provided within an appropriate container. A spark gap or arc generated within the sample with an appropriate fiber optic cable coupled directly to transmit the output of the atomic light emission. Although the exact phenomena occurring is not presently thoroughly understood, it is believed that a gas plasma in the exerted intern of portion defines a liquid-contained pocket encapsulated and confined within the liquid medium or solution.

In a practical system for either an on-line system or a sampling system, a light transmitting fiber optic cable has its finished end coupled to the electrical discharge gap and establishes an output signal containing the several wavelengths of the elements in the solution which is impressed on a spectrograph unit. A suitable grating directs the dispersed light signal in a spectral pattern which is conveniently detected by a suitable sensitive detector array such as a linear serial photodiode array to produce related electric signals. The integrated signals are serially transmitted to a suitable processor such as a microcomputer in a plurality of scans. The microcomputer processes the data to provide the atomic spectrum of all of the elements in the liquid solution to provide the atomic specter of all of the elements in the liquid solution.

The concept of on-line spectrometry has great application in monitoring a broad range of metal elements in liquids for various industrial applications such as metal plating, electronics, steel making and processing and environmental control industries as well as various others where the analysis of metals or other elements in a material is required. The present invention will of course also have significant usage in laboratory environments because of the speed of analysis as well as the convenience.

BRIEF DESCRIPTION OF THE DRAWINGS

The drawings furnished herewith follows a preferred embodiment of the invention presently contemplated by the inventor. In the drawings:

FIG. 2 is an exploded view of an optrode unit shown diagrammatically in FIG. 1;

FIG. 3 is a block diagram of dual power source for the system shown in FIG. 1; and FIG. 4 is a view showing a similar atomic emission spectrometry system for treating individual liquid samples.

DESCRIPTION OF ILLUSTRATED EMBODIMENTS

Figure 1:
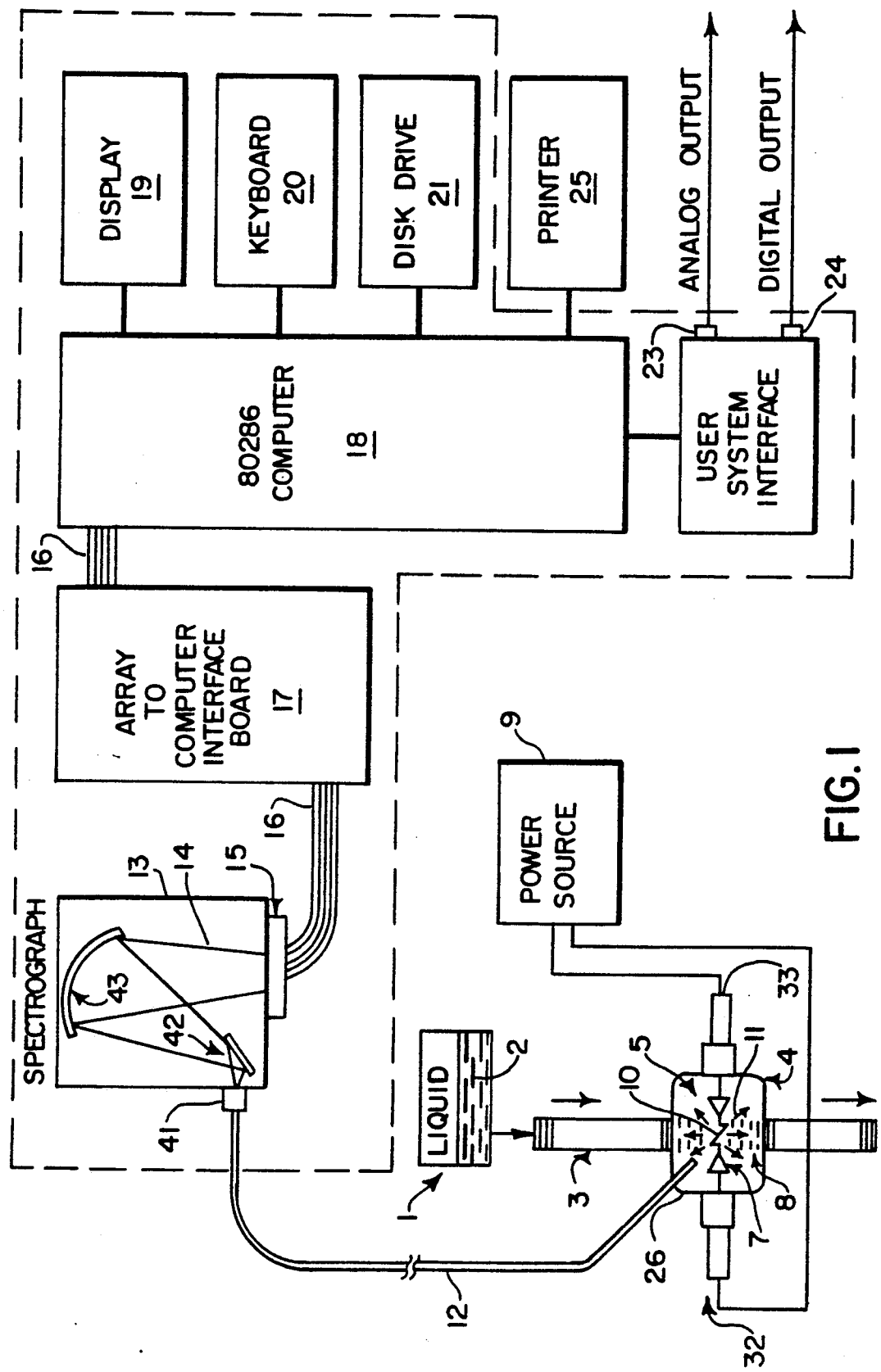
FIG. 1 is a block diagram of an atomic emission spectrometry system illustrating an embodiment of the present invention.

Referring to the drawings and particularly to FIG. 1, atomic emission spectroscopic instrument 1, constructed in accordance with the teachings of the present invention, is illustrated for analyzing a liquid 2 flowing through a line 3. The instrument 1 includes a flow through optrode unit 4 having an internal excitation chamber 5. The optrode unit 4 includes a flow-through passageway including the chamber 5 connected in line 3. An electrical discharge gap unit 7 is secured within the chamber 5, and particularly the liquid 8 flowing therethrough. A power source 9 is coupled to the gap unit 7 for generating of an electrical discharge, shown diagrammatically at 10, within the gap unit and particularly liquid 8 within the chamber 5. Unit 7 is operative to excite the atomic elements within the liquid in the chamber and create atomic emission light, shown diagrammatically at 11, related to the elements in the liquid solution.

A fiber optic cable 12 couples the emitted light 11 within the liquid 8 to a spectrograph 13 which is operable to separate the several element-related wave lengths of light into a dispersed beam 14. The illustrated spectrograph system 13 was developed by the assignee of this application for various other applications and is readily coupled through the fiber optic cable 12 to the submerged gap unit 7. The separated or dispersed beam 14 is impressed on a detector array 15 to generate proportional electrical signals. An array cable 16 and an interface board 17 connect the signals to a logical signal processor such as a programmed computer 18. The computer typically is constructed, in accordance with conventional technology, with an appropriate display 19, keyboard 20 and a disk drive 21 as well as a user system interface for outputting of an analog signal via a port 23 or a digital signal via a port 24. A printer 25 is also coupled to the computer to permit selective or total print out of the analysis.

More particularly, the optrode unit 4, as more clearly shown in FIG. 2, includes a head 26, shown as a block member, including an internal chamber 5 formed by cylindrical opening 27 in the head. The opening is closed by closure plates 28 bolted to the sides of the head 26. The closure plate 28 include suitable windows 29 formed of a fused silica or other suitable material. Flow line connecting openings 30 and 31 in the head 26 are connected to the line 3. Electrical discharge electrodes 32 and 33 are mounted within the head 26 in the end walls of head 26. The electrodes terminate in appropriately spaced relation within chamber 5. Each electrode 32 and 33 is similarly formed and includes a suitable stainless steel conductor 34 having o-ring seals 35 to sever the electrode in the end wall. An electrode tip 36 is secured to the end of conductor 34 within chamber 5. A power source connector 37 is clamped to the outer end of the conductor by suitable clamping bolt 38 for supply power from source 9 to the electrode tips 36 for generating the electrical discharge within the chamber 5. The electrical discharge between the electrode tips 36 excites the liquid solution and particularly any element within the liquid to produce atomic emission in accordance with such elements in the solution.

The fiber optic cable 12 and is sealed within an opening wall of the head 26 with a flat sensing end 40 exposed to the electrical discharge 10, and thus the related atomic emission light of the elements. The atomic emission light is of a frequency related to the specific elements, and the emitted signals are transmitted by the fiber optic cable 12 to the spectrograph 13.

The illustrated spectrograph 13 includes a fixed image grating system. The cable 12 has its terminal or output end 41 aligned with a dispersion mirror 42 which directs the light beam 43 onto a curved grating unit 44, which in turn redirects the individual light signals onto a detector array 15.

The detector array 15 may be a standard self-scanning silicon photodiode array unit. The photodiode detector array 35 transmits the individual wave length signals through the computer interface board 17 to the computer 18. The computer individually processes each of the wave length signals and provides a composite output signal which can be displayed to indicate the relative level of the various elements in the sample. An Intel 80286 processor may be used to analyze the results and data from the linear photodiode detector array 15. The computer processing of the signals from the array may use any suitable known program and will be readily provided.

The electrical discharge may involve creation of either a spark discharge or an arc discharge depending on the particulars of the elements and the purpose of the analysis. The power system for creating other electrical discharge are well known and discussed in the previously identified publication by Prentice Hall and a detailed system is not therefore given.

For selective application to various specifications, a dual supply system can be provided, for example, as shown in FIG. 3 wherein a spark generator 45 and an arc generator 46 are shown coupled to a single power control unit 47 for selective connection and use of either generator. The output of the generators are connected through a suitable common or summing connector 47a to the electrodes 32 and 33 of the optrode unit 4 and particularly, the electrode connectors 37. The power control unit 47 provides for selection and appropriate outputs from the selected generator, the appropriate voltage and current controls are shown. The spark generator generally provides a direct current (D/C) sparks as the electrical discharge while the arc generator will provide an alternating current discharge. Because of the high energy power levels required, suitable electronic switching devices are used in accordance with known practice. Whether the spark generator or the arc generator is used to generate the electrical discharge, an appropriate repetition rate control signal is established as at 48a. Separate spark current and arc current controls establish the intensity of the respective electrical discharge between the electrodes, as at 48b and 48c. In addition to the repetition rate and the current level, a duty cycle control 49 is coupled to the arc generator 46. The control particulars are readily provided by the making of generators. Atomic emission analyzing apparatus of this invention may normally be designed with a particular power supply for purposes of economy of construction unless a wide variety of applications are contemplated by the user.

Actual experimental results using a sampling system as shown in FIG. 4 and presently described have established the capability of the direct liquid excitation system to produce atomic emission for spectrometric analysis.

In FIG. 4, an open top container 50, such as a conventional beaker, is filled with the liquid solution 51 containing one or more elements known to have specific atomic emission frequency or wavelengths. An electrical discharge gap unit 42 is mounted within the container 50 and connected to a suitable power supply 53. The known spectrometry system as shown in the first embodiment was used with the sampling system. The fiber optic cable 54 extends through the upper surface of the liquid solution 51 into close spaced relation to the discharge unit 53. Generally, a spark within the liquid solution resulted in excitation of the elements in the solution with specific elemental-related atomic emission within the liquid. The atomic emission, in the form of light, is coupled to the fiber optic cable 54 for coupling into the spectrograph system 55.

The integration time of the photodiode detector array 35 will typically be on the order of 0.1 seconds. A series of 10 to 50 such scans can be made in about 1 to 5 seconds, and provide a typically periodic timing and scanning basis depending upon the dynamics of the atomic emission under consideration.

The graphical illustrations of FIGS. 5–12 illustrate traces generated by the apparatus of FIG. 4. The results of the materials analyzed are summarized as follows.

Figure 5:
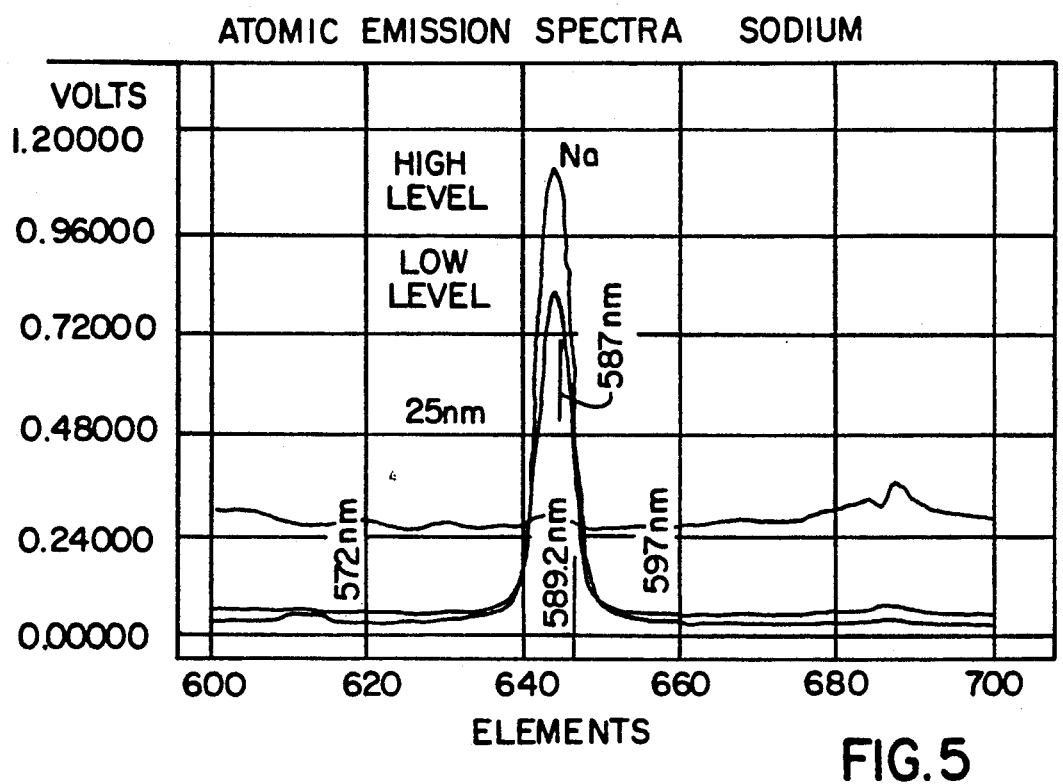
FIGS. 5-14 illustrate output of the system shown in FIG. 4 for various liquid solutions.

Sodium - FIG. 5

The LAES sodium spectra at the 589.2 nm band are shown for two different levels of sodium.

Figure 6:
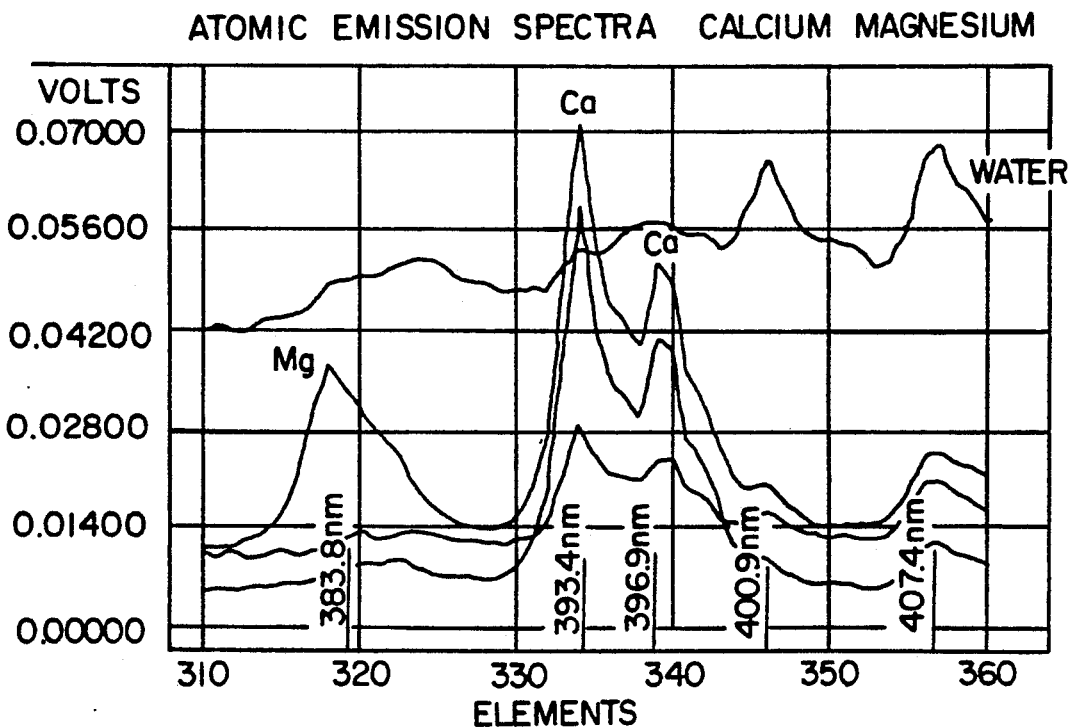

Magnesium, Calcium - FIG. 6

Calcium peaks at 393.4 nm and 396.9 nm are shown at different concentration levels along with magnesium at a single level at 383.8 nm. The concentration range for calcium is 200–400 ppm. The magnesium plot includes the high end solution of calcium.

Figure 7:
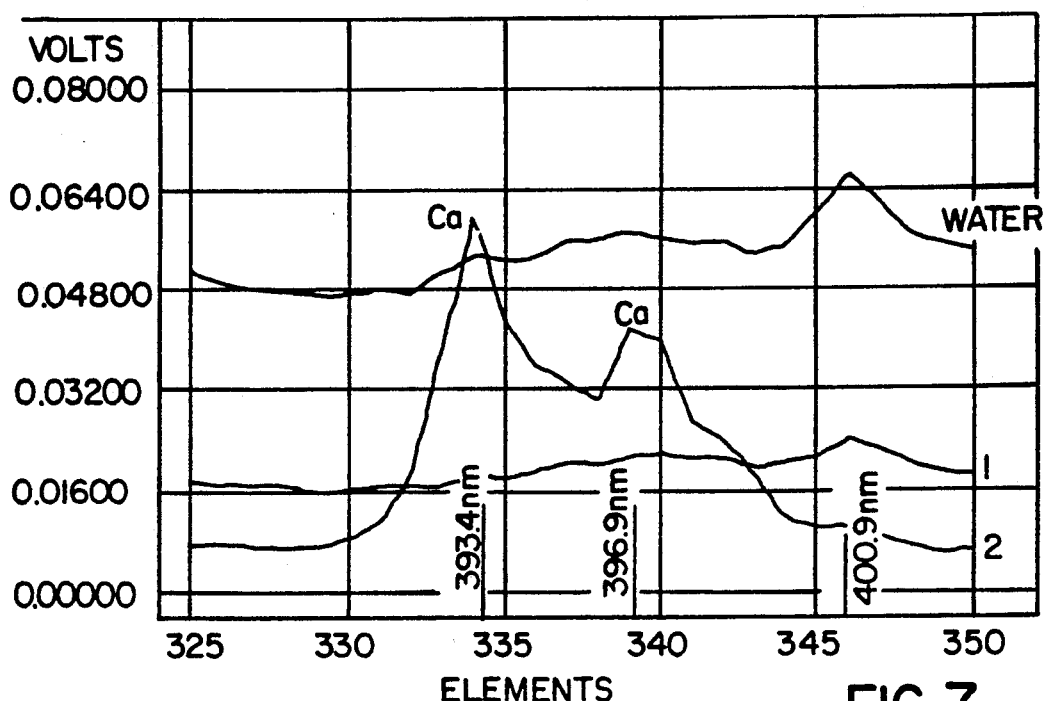

Calcium - FIG. 7

Calcium is shown again in the 393.4 and 596.9 nm bands.

Figure 8:
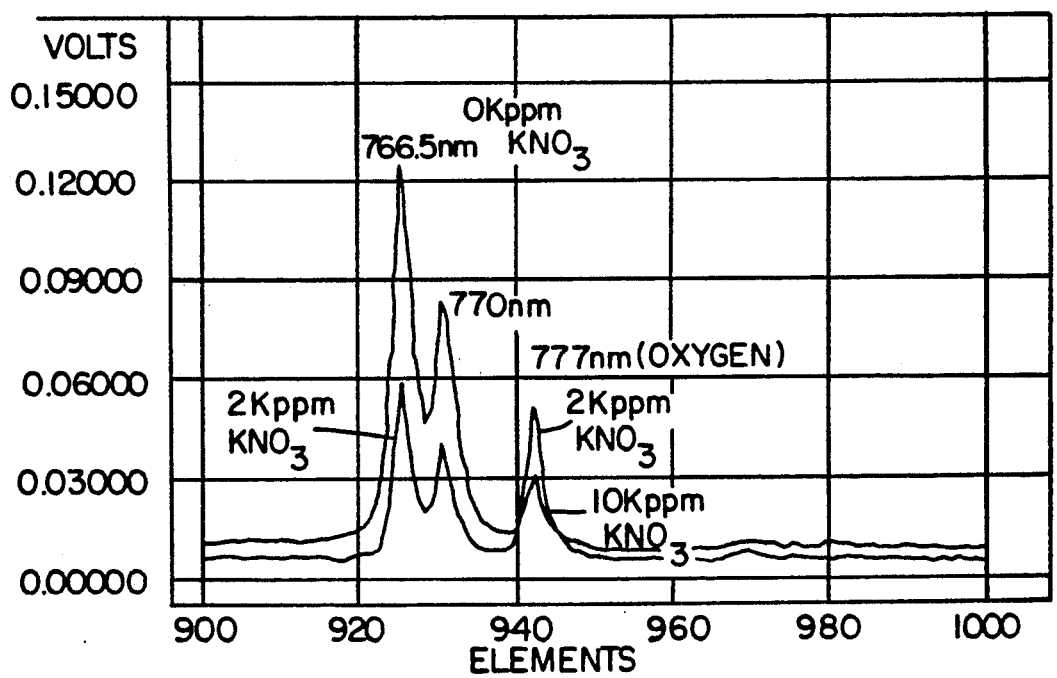

Potassium - FIG. 8

Potassium is shown as a doublet at 766.5 nm and 770 nm at two different concentration levels.

Figure 9:
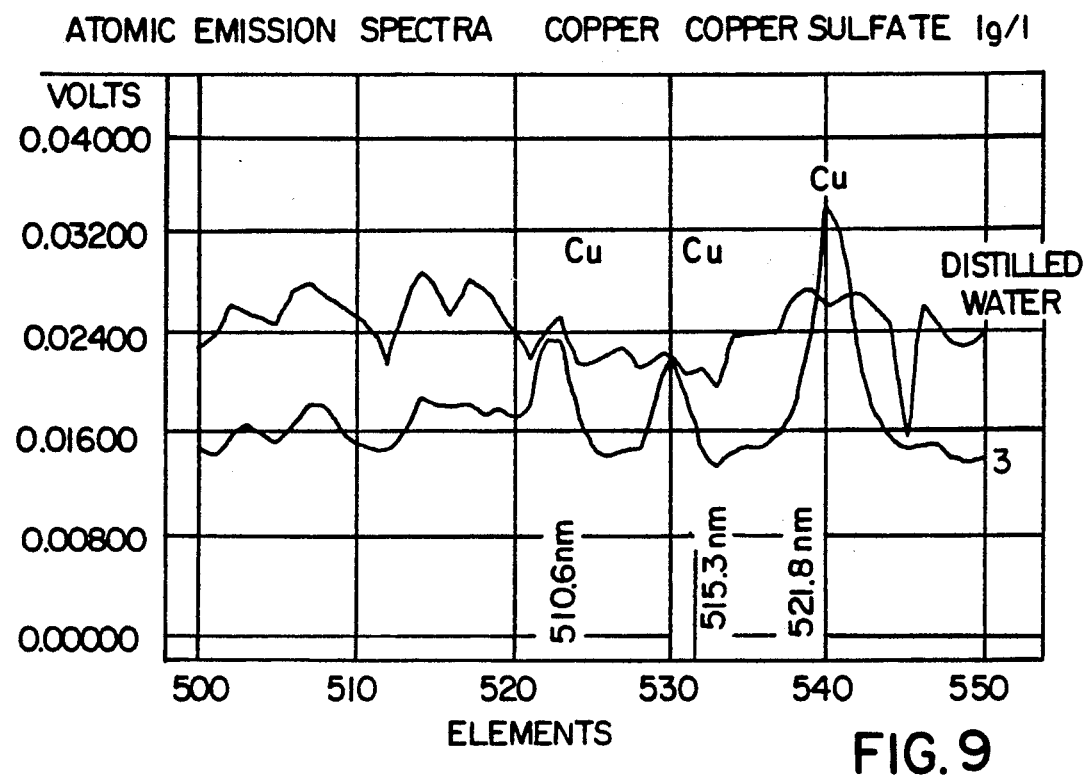

Copper - FIG. 9

Copper spectra are shown at three wavelengths (510, 515, 522 nm).

Figure 10:
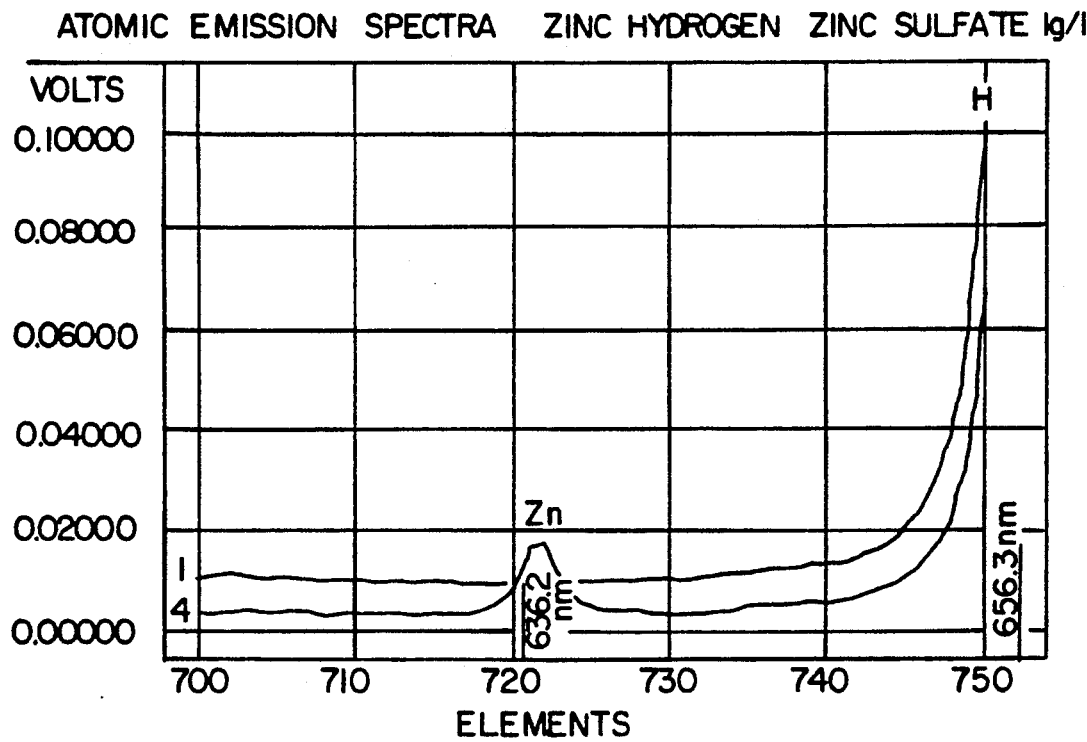
Figure 11:
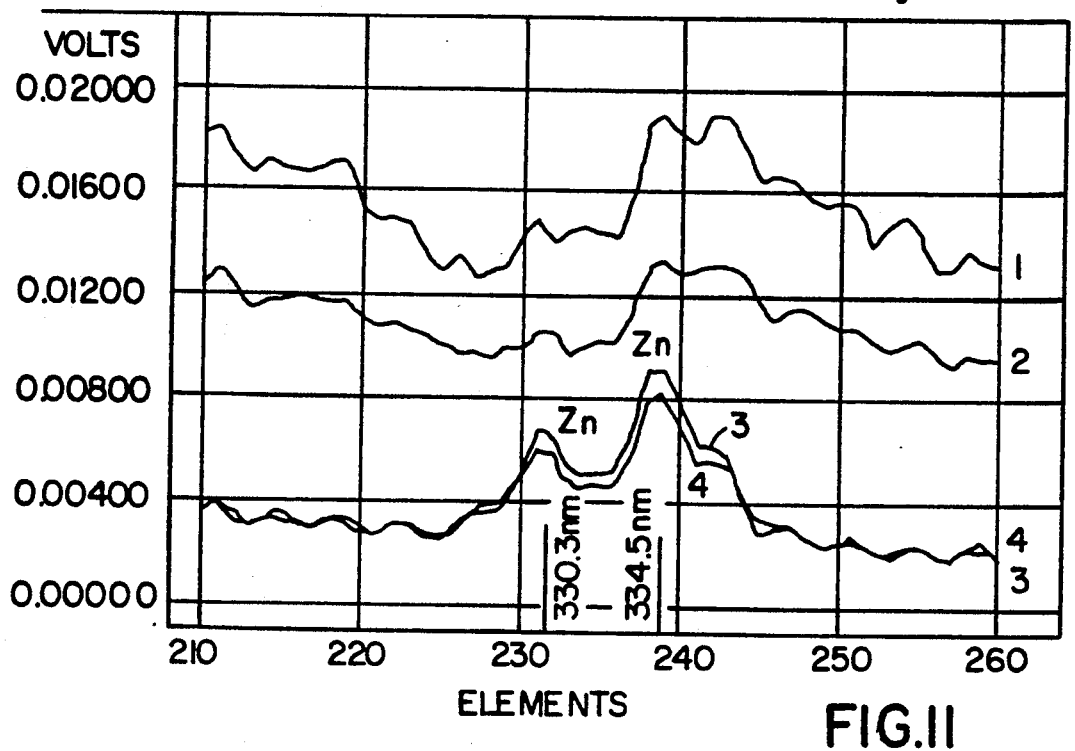
Figure 12:
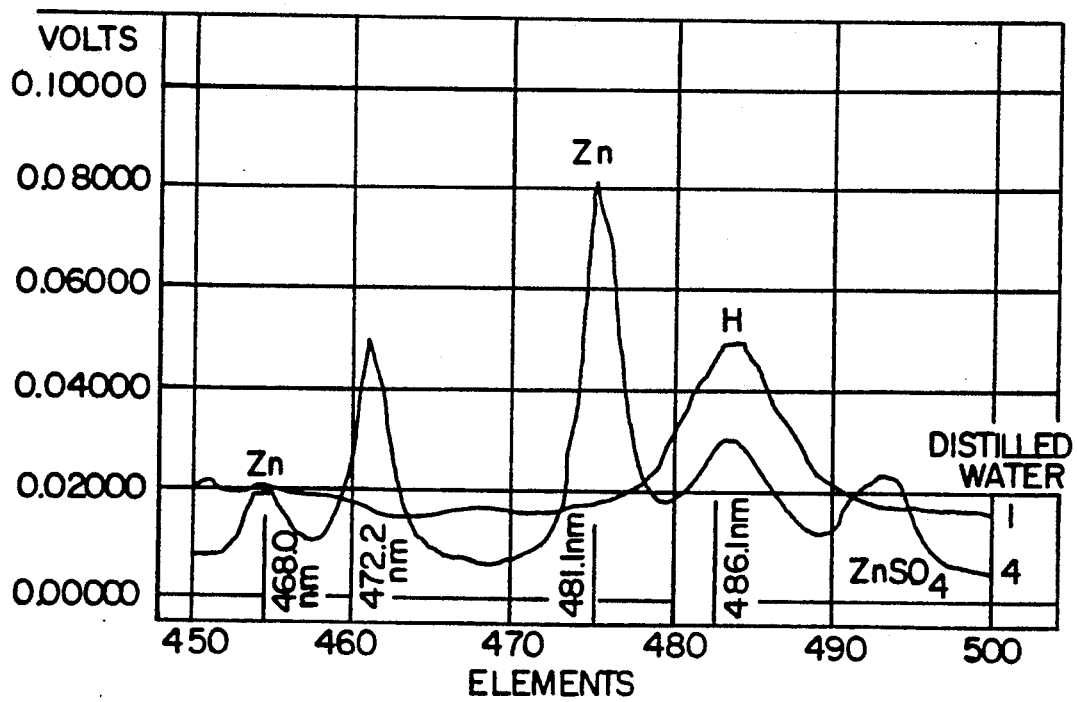

Zinc - FIG. 10-12

Zinc is shown in FIGS. 21, 22 and 23 at a series of six wavelengths from 330.3 to 636.1 nm. The 3p to 2s hydrogen line in water is evident at 656.3 nm.

Figure 13:
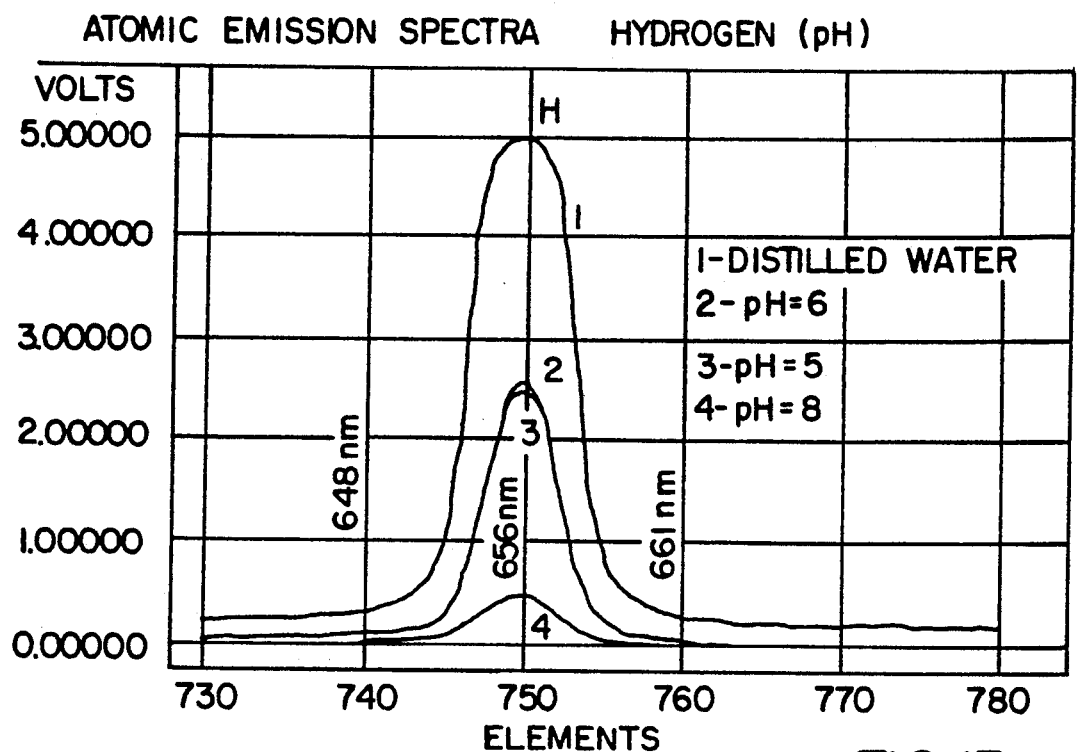

Hydrogen and pH - FIG. 13

Changes in the hydrogen line at 656.3 nm with changes in pH are shown. Interactions occur that complicate the pH relationship, but there is a potential for using the hydrogen line to measure pH.

Figure 14:
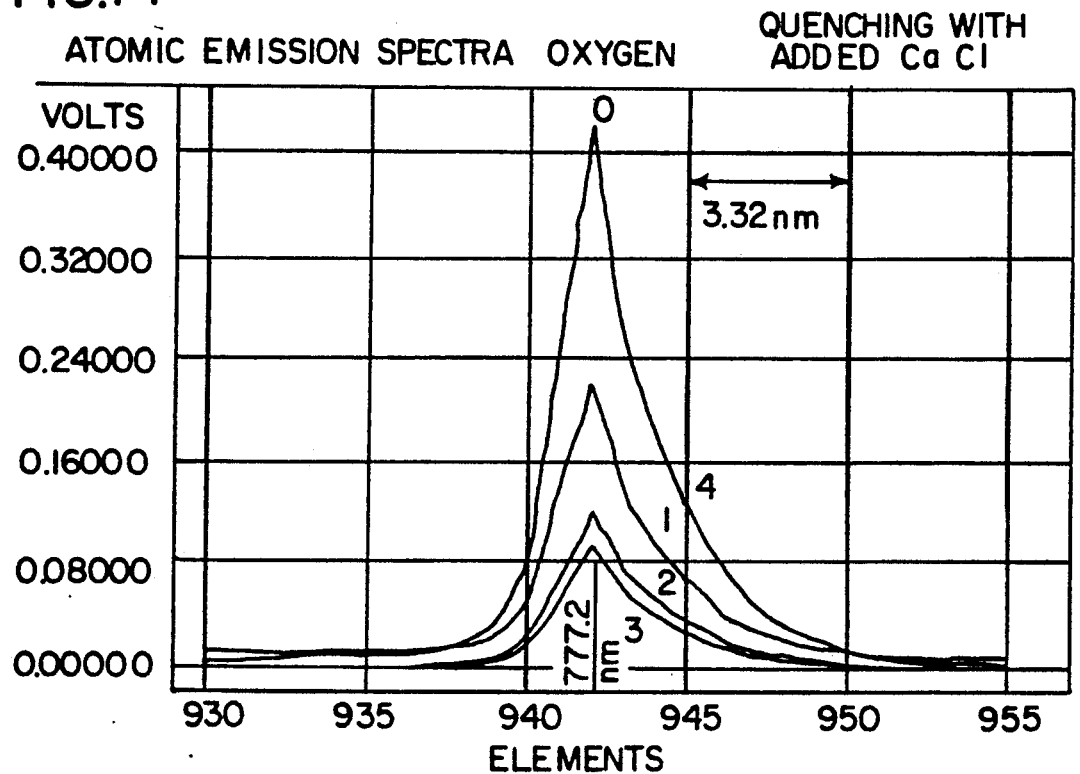

Oxygen - FIG. 14

The oxygen line at 777.2 nm in water is illustrated at varying pH levels along with other atomic spectra. Future studies are necessary to correlate oxygen line amplitude and oxygen concentration in nutrient solutions.

The present inventor has carefully analyzed and conducted various tests involving the new technology of this invention and recognize areas will require refinement and attention to provide the optimum characteristics including sensitivity, repeatability and resolution.

Advantageously, the system is built with the degree of sensitivity and repeatability to provide an output identifying the presence of the atomic element or elements in the liquid solution. Theoretically, a spark will provide a greater sensitivity because of the characteristic of generating the spark in a very short time. However, it is well known that the spark system does not provide a high level of repeatability.

If the precision and sensitivity ability of the system or apparatus does not provide reliable quantitative result, the output may be used for a qualitative or semi-quantitative output.

Also, the output for certain atomic elements may have close spaced double peaks, for example, potassium and sodium. The liquid tends to merge the peaks and thus interfere with the resolution. In connection with qualitative and quantitative determination as to the presence of elements in a liquid solution, the resolution may not be particularly significant. However, in analyzing a liquid solution having a plurality of elements, two of the elements may have atomic emission wavelengths relatively close and resolution may become very quite significant. Further, in analysis of a molecule, resolution may be significant. Generally, presently known and used decomvolution systems will sharpen the resolution of the spectrographic output.

Although one may prefer to correct the resolution using an inexpensive hardware, the system may require certain compromises for such a solution. If the compromises are not acceptable, computer-based decomvolution will be used to sharpen and distinguish the signals.

The graphical illustration of the results obtained with this simple fixed container analyzer illustrates the significance of the generation of the output by forming of the analysis directly within the gas. Liquid atomic emission spectrometry thus provides a very effective and rapid means for analyzing of liquid mediums for the elemental constituency in the liquid medium. Various well known basic analysis equipment is available which can with further modification improve the results obtained with this invention. Thus, the output of the present invention provides a finally helpful information content for the use of improved optical resolution in sensitivity to particular bands or spectrum related to particular materials. This very low parts per million have been detected using wide band optics indicating that with a set resolution changes the apparatus can provide sensitive detection from micromolar chemical solutions that are on-line or in the batch processes. Further, the system is readily adapted to commercial processing applications as well as to laboratory analysis.

Various modes of carrying out the invention are contemplated as being within the cope of the following claims particularly pointing out and distinctly claiming the subject matter regarded as the invention.

I claim:

1. A method for directly analyzing liquid solutions for an atomic element having known atomic emission of a known wavelength, comprising containing a liquid solution in a confining sensing unit, generating a confined electrical discharge within said solution with said electrical discharge totally enclosed by said liquid solution, sensing the light wavelengths of the electrical discharge within the liquid solution, said electrical discharge exciting the atomic elements in said liquid solution and creating an atomic emission spectrum within said confined electrical discharge related to the atomic elements in such solution, coupling said atomic emission spectrum to a spectrograph to provide spectral pattern signals proportional to spectral pattern of different wavelengths in said atomic emission spectrum, said spectral pattern signals including quantitative information as to the level of each atomic element in said solution, simultaneously detecting and recording the different wavelength signals of said atomic emission, rapidly repeating said generating of said electrical discharge and said simultaneously detecting and recording of said atomic emission within about five seconds, and simultaneously processing of said different wavelengths in said original and repeated signals for determining the quantitative elemental content of each of said atomic elements within said liquid solution and thereby establishing a composite output signal including the relative level of said content and reflecting the interaction between the several atomic elements.

2. The method of claim 1 including continually passing the liquid solution through said sensing unit, said generating step including maintaining an arc within said liquid solution and generating said atomic emission.

3. The method of claim 1 including continually passing the liquid solution through said sensing unit, said generating step including creating a series of timed spaced sparks within said liquid solution and generating said atomic emission.

4. The method of claim 1, 2 or 3 wherein said coupling step includes coupling a fiber optic cable to said electrical discharge within said liquid solution closely adjacent the electrical discharge, and connecting said fiber optic cable to said spectrograph.

5. The method of claim 1, wherein said sensing unit includes an enclosed chamber having an inlet and an outlet, and including passing said liquid solution in a controlled flow through said chamber, as a continuous stream, and generating said electrical discharge as a series of time spaced electrical discharges.

6. The method of claim 5, wherein said electrical discharges each include an electrical spark.

7. The method of claim 5 wherein said electrical discharges each include an electrical arc.

8. A liquid analyzing apparatus, comprising a chamber unit for confining a liquid solution, electrical means repeatedly exciting an enclosed internal portion of said liquid solution with essentially identical currents and periods in a sequence of immediately following excitations and each excitation generating an excited internal portion totally enclosed within said liquid solution and thereby produce an atomic emission spectrum of light in said excited internal portion of the liquid solution and generate a related spectrum of wavelengths identifying each of the atomic elements in said liquid solution during each said excitation, and a sensing unit close coupled to the enclosed internal portion of said liquid for detecting said spectrum of light, a light transmitting unit coupled to said spectrum of light, and a spectrum analysis apparatus connected to said transmitting unit and operable to simultaneously detect and record signals of the intensity of the different wavelengths in each excitation and simultaneously processing said signals to establish an output reflecting the interaction between the atomic elements and produce a quantitative readout of the atomic elements within said solution.

9. The analyzing apparatus of claim 8, including means for passing said liquid solution in a flow path through said chamber unit simultaneously with said exciting of the solution, said means for exciting said liquid solution in said enclosed inner portion including an electrical discharge source located in said internal portion and creating an electrical discharge totally enclosed by the liquid solution passing through said chamber unit.

10. The liquid analyzing apparatus of claim 9, wherein said mans for exciting the liquid solution includes a pair of opposed and spaced electrodes, a high energy power source is connected to said electrodes to create a high energy electrical discharge in said internal portion of the liquid solution and thereby generate said related spectrum of light.

11. The analyzing apparatus of claim 10, said means for exciting said solution intermittently activates said high energy power source for creating time spaced electrical discharges in said internal portion of the liquid solution passing through said chamber unit.

12. The apparatus of claim 11, wherein said electrical discharges include time spaced sparks.

13. The apparatus of claim 11, wherein said electrical discharges include time spaced alternating current arcs.

14. The apparatus of claim 8, wherein said sensing unit includes a fiber optic cable coupled to said excited solution and establishing an output signal containing the several wavelengths of the atomic elements in the solution, said transmitting unit including a light dispersion unit coupled to said cable and forming a dispersed light signal in a spectral pattern, said analysis apparatus including a light sensitive detector array producing integrated elemental signals for each of said atomic elements, and processing said elemental signals to provide a quantitative output for each of the atomic elements in the liquid solution.

15. The method of claim 14, wherein said fiber optic cable includes an input end located within the chamber unit immediately adjacent the location of the electrical discharge and exposed directly to the electrical discharge within said solution.

* * * * *

UNITED STATES PATENT AND TRADEMARK OFFICE
CERTIFICATE OF CORRECTION

PATENT NO. : 5,278,629

DATED : January 11, 1994

INVENTOR(S) : KENNETH J. SCHLAGER

It is certified that error appears in the above-identified patent and that said Letters Patent is hereby corrected as shown below:

Claim 10, col. 8, line 22, delete "mans" and substitute therefor ---means---;

Signed and Sealed this

Twenty-ninth Day of November, 1994

*Attest:*

BRUCE LEHMAN

*Attesting Officer*     *Commissioner of Patents and Trademarks*